US006610840B2

(12) United States Patent
Sonnewald et al.

(10) Patent No.: US 6,610,840 B2
(45) Date of Patent: Aug. 26, 2003

(54) METHOD OF ISOLATING A MESOPHYLL-SPECIFIC PROMOTER

(75) Inventors: Uwe Sonnewald, Hoym (DE); Marcus Ebneth, Quedlinburg (DE); Ralf-Michael Schmidt, Neustadt (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 25 days.

(21) Appl. No.: 09/799,895

(22) Filed: Mar. 7, 2001

(65) Prior Publication Data

US 2002/0120955 A1 Aug. 29, 2002

Related U.S. Application Data

(62) Division of application No. 09/284,418, filed as application No. PCT/EP97/05900 on Oct. 24, 1997, now Pat. No. 6,229,067.

(30) Foreign Application Priority Data

Oct. 25, 1996 (DE) ........................................ 196 44 478

(51) Int. Cl.[7] ........................ C12N 15/29; C12N 15/82; C12Q 1/68

(52) U.S. Cl. ...................... 536/24.1; 800/278; 800/287; 435/6; 536/23.6

(58) Field of Search ................................ 800/287, 278; 536/24.1, 23.6; 435/6

(56) References Cited

U.S. PATENT DOCUMENTS 6,229,067 B1 * 5/2001 Sonnewald et al. ......... 800/287

OTHER PUBLICATIONS

Fourgoux–Nicol et al, Isolation of rapeseed genes expressed early and specifically during development of the male gametophyte, 1999, Plant Molecular Biology, vol. 40, pp. 857–872.*

Kim et al, "A 20 nucleotide upstream element is essential for the nopaline synthase (nos) promoter activiity", 1994, Plant Molecular Biology vol. 24, pp. 105–117.*

* cited by examiner

*Primary Examiner*—Elizabeth F. McElwain
*Assistant Examiner*—Medina A. Ibrahim
(74) *Attorney, Agent, or Firm*—Keil & Weinkauf

(57) ABSTRACT

The present invention relates to a method of isolating a promoter, which causes, in plants, permanent Mesophyll-specific expression of an operably linked encoding nucleotide sequence, for example a sequence which imparts resistance or an increase in the photosynthetic performance.

1 Claim, 12 Drawing Sheets

GGATCCAGCTAATGCTGCTCTTGTCACTCAAAATGATGGTATCCCTCTCGTCATCCAGTGTTTGTCAAG
TCCTGTTAGGAACACAGTAAGGATATAAACAAACATTTTGTGGTCTTCTTGGTTATTGAGTGCTTGCTGTTCACT
TGTTAAAATTGCACATATACGTAGTGAGAAACTCAACTGTTGAGTACCATTGATCCGTCAATCTTGTCGATAACT
TTGATAAGGATATTTCAGGCATCAGACATGTCACCTCTATAGAACTTGGTCTTTTTTTTTAAAAATAAAAATAAA
AATGTTTGGCATCATACGAACTTCTGTTACTTTAGGCTGTATCCAGAATAAAATGTTGTTTCCTCATTCTGGAAT
TAGTTGTTTTGCACACGGAAGACTTTCGAAATTTACTAATTGTGTTCGTCCGTCTCAAACTGGCTCACACTTTGG
TGGTCAATTTTACTTCTCAAGGTAAGCAATTACAGAATATGAATGTCGCTCTCCTCATATTTATCCGAACAATAA
AAAATGATATCTGTTTGCATATGCATGTAGATCACACACCCCCCCCCCCCCCGCCCCTAGATTCCCTCGATTTAG
ATTAAATATAATCATCTACAAGAATTCCGTTGGGCTTCATTATGTGTTTTTACATATTCGTTTCTGAACCACCCC
CACCCCGGTGAAAAACATTGCTCTGCCACTGGCTCAATGTATTGACACAAATGAACTTCAAACTGGGCAGGTGAA
TTATGCTCTAGGAGCATTGTATTATCTATGCAATGCATCAAACAAGGAAGAGATCTTAAAGCCAGAAGTAATTGA
TGCAATCAAAAGTTATGCAGCTGCAGGTGGAGTTAGTACAAGCTTCAGTAATTTGGCTCAGGCTTTCTTAGATCA
ACATGTTCCTCAGCTTAATTAAAATGGAGGAAACCAAAGATTATGTTGTAAAATCATTTTCTATCCTAGATGGTC
TATCGGAAACAATTTATTTATTACTCCTATCCAATTCATTATATTTTCAAAAGTTATGAAGTCCACGAAATATGT
GACGTGGGTAAAGAAGACCCATGCCAAGCCAGTGGGATATAGAAACAAAACATGTAATAAAGAGAACAAATAATG
AGTTTCGAAAAGAACAGAAGTTAGCATAAGGACGAGAATCACATTATCTTAGGTGCCAACCACTAATCCTATGTA
TCATTCTCCTCTTTCCACGTGTCATCCTACACTTCCTTTGCCATCAGATTAGATAGCCCGGTTAGTACCTACACT
GTATATCAAAAAATACGTAACAATCATCCAAACATATCATCGATCAAAGGATATTTATCTTGATGTGCTTTCGCC
GTCCATTGTAACGAGTTTGGATGAATTTGATATACACCCACTCAGATATCAATATATTTTATAAAAAGAAACAAA
ATTGAATACTAGTAATATCTATGTAGATATTTATTTTTTCAACAATCCTGTAAGTTATAAGGATAACTCACTTAT
ATGTGACGTGGATAATGAAGAGCTAGGCAGGCAGTGAGAGATAGAAACAAATTAAGCAGAGACGAAAAACAAATC
AGTTAACAGAATGACGAATTGGATCACGCTTTATCTTAGTGCCAACCACTGATCCCATGCATCACTCTGCTCTTT
CCACGTGGCATCCTCTGACGTCAGATCAGATTCCTCTTCTTTCTTTTTTTTTTCTGTATATATATGAGCATTTTA
GTAGT

FIG. 2

1: source leaf

2: sink leaf

3: stem

4: root

5: seed

```
aaatcagtta acagaatgac gaattggatc acgctttatc ttagtgccaa ccactgatcc      60
catgcatcac tctgctcttt ccacgtggca tcctctgacg tcagatcaga ttcctcttct     120
ttcttttttt tttctgtata tatatgagca ttttagtagt actgcgtgcc caatctctta     180
cataaaaatc gaagcacgat ggatcacgcg gcggatcgac accggacgga tttgatgaca     240
ataacaaggt ttgtgttgaa tgagcagacg aagcaccctg aatcccgtgg agacttcagt     300
attttgctca gtcacattgt tcttggctgc aagttcgtat gcactgctgt taacaaggca     360
ggtttagcca aacttctagg acttgctggt gagactaatg tgcagggaga agatcaaaag     420
aaacttgatg tactctcaaa tgaagtgttt atcaaggctt tggttagcag taaccgaaca     480
tgcattcttg tctctgaaga agatgaagaa gccacatttg ttaggccagc taaccgtgga     540
aaatactgtg tagtttttga tcctctggat ggatcatcga acattgattg tggtgtttct     600
attggaacga tctttggaat ttacatgatc aaagacggtc atgaaccaac actagatgat     660
gtcttgcaac ctgggatgaa catgttagct gctggttact gcatgtatgg aagttcttgt     720
acgctagttt tgagcactgg atctggagtt aatggtttta cccttgatcc ctctcttggc     780
gagttcatcc taactcatcc tgacatcaag attcctaaga aagggaagat ttattcagtg     840
aatgaaggaa atgccaagaa ctgggacagt ccaacatcca aatatgtgca gagctgcaag     900
tatcccgctg atggttcttc accaaaatct ttgagatata ttggaagtat ggttgctgat     960
gttcatcgta cattactcta tggaggcatc ttcttgtacc ccggagataa gaaaagcccc    1020
aacgggaaac tgagggttct ctatgaagta tttcccatgt catttctgat ggaacaagca    1080
ggaggccaag catttactgg gaagcaacgg gcacttgact tagttccaga gaagatacac    1140
gaacgctctc ctatatttct tggtagttat gatgatgttg aggagatcaa aaagctctac    1200
gctgctgaag agcaaaactg atagatgtat ctataccatg taatcacttc actactcttg    1260
ctggtgcaga tatcaaattt ctcaaattac agcaagttgt tactgtttat gttgcacaat    1320
agctgctgtg atgcgataat acgttcacat tactggttgt tctaactttt tgtcttgaag    1380
tatctatttc tcatcaacaa taaaatgttg aatagagaag ttctggctta ttattgttat    1440
caaagttctt ttgtaatgtc atccatttag aatcaagcta attttt                   1487
```

FIG. 10

METHOD OF ISOLATING A MESOPHYLL-SPECIFIC PROMOTER

This application is a divisional of Ser. No. 09/284,418, filed on Apr. 14, 1999, now U.S. Pat. No. 6,229,067, which is a 371 of PCT/EP97/65900 filed Oct. 24, 1997.

BACKGROUND OF THE INVENTION

The present invention relates to nucleic acid sequences having promoter activity, which cause a leaf-specific expression, in plants, of encoding nucleotide sequences under the control of said promoters, to expression cassettes, recombinant vectors and microorganisms which embrace such regulatory sequences, to transgenic plants transformed with them, to a method of producing transgenic plants, and to a method of isolating the leaf-specific promoter.

It is known to transfer foreign genes into the genome of a plant in a targeted manner by means of genetic engineering methods. This process is termed transformation, and the resulting plants are termed transgenic. Transgenic plants are currently employed in various fields of biotechnology. The predominant aims are, on the one hand, crop protection and, on the other hand, an improved quality of the harvestable products. In order to express foreign genes efficiently in plants, regulation signals which allow ordered transcription are required. These include promoters and terminators. The terminators located on the 3' end of the encoding DNA serve to end transcription and, if appropriate, as a signal for polyadenylation of the mRNA formed. Promoters contain recognition sequences for RNA-polymerases and for transcriptional effectors. The promoters are responsible for the expression behavior of the foreign genes.

Herbicide-tolerant plants as they are disclosed in DE-A-3701623 are an example of genetic engineering measures in crop protection. Other examples are insect-resistant plants (Vaek et al. (1987) Plant Cell 5, 159–169), virus-resistant plants (Powell et al. (1986) Science 232, 738–743) and ozone-resistant plants (Van Camp et al. (1994) BioTech. 12, 165–168). Examples of quality improvements achieved by genetic engineering are: better keeping qualities in fruit (Oeller et al. (1991) Science 254, 437–439), increased starch production in potato tubers (Stark et al. (1992) Science 242, 419), altered starch (Visser et al. (1991) Mol. Gen. Genet. 225, 289–296) and lipid composition (Voelker et al. (1992) Science 257, 72–74) and production of plant-foreign polymers (Poirer et al. (1992) Science 256, 520–523).

A large number of promoters which control expression of foreign genes in plants is known. The most frequently used promoter is the 35S CaMV promoter (Franck et al. (1980) Cell 21, 285–294).

This promoter contains various recognition sequences for transcriptional effectors which, in their totality, lead to constitutive expression of the gene which has been introduced (Benfey et al. (1989) EMBO J. 8, 2195–2202). Frequently, inducible or cell- or tissue-specific promoters are also employed.

Examples of inducible expression which have been described are, inter alia, the following: wound induction (DE-A-3843628, DE-B-3837752), chemical induction (Ward et al. (1993) Plant Molec. Biol. 22, 361–366) and light induction (Fluhr et al. (1986) Science 232, 1106–1112).

DE-A-4207358 discloses a promoter which causes gene expression specific to the stomatic cells, but no specific expression in mesophyll cells or in epidermal cells of leaves. An artificial change of the opening periods of the stomata allows the gas exchange of plants manipulated in this fashion to be regulated as desired. Herbicide tolerance or herbicide resistance can not be mediated by such a promoter.

Other examples of cell- and tissue-specific expression are: seed-, tuber- and fruit-specific expression (compiled in Edwards and Coruzzi (1990) Annu. Rev. Genet. 24, 275–303; DE-A-3843627), phloem-specific expression (Schmülling et al. (1989) Plant Cell 1, 665–670), root-nodule-specific expression (DE-A-3702497) and meristem-specific expression (Ito et al. (1994) Plant Molec. Biol. 24, 863–878). Examples of promoters in chloroplast-containing cells are also known from Edwards and Coruzzi (1990), Annu. Rev. Genet. 24, 277–279. The promoters described in this publication cause expression either only in inducible form (for example the rbcS-3A promoter) or only in certain types of cells (for example the GS2 and GS3A promoters), but the expression is not limited to certain parts of the plant.

The use of the above-described promoters is frequently problematic. For example, promoters which cause constitutive expression of the genes under their control can be employed for generating herbicide-tolerant and pathogen-resistant plants, but have the disadvantage that the products of the genes under their control exist in all parts of the plant, including the parts of the plant which are harvested, which may be undesirable in some cases. Equally, inducible promoters are not without problems since the conditions for induction in crop plants are typically difficult to control in the field.

In C3 plants, the promoter of phosphoenol pyruvate carboxylase, which originates from a C4 plant, leads to expression in the mesophyll-of the leaf (Stockhaus et al., (1994), Mol. Gen. Genet. 245, 286–293). However, this promoter only mediates a low activity level in the mesophyll. Moreover, it also shows activity in roots. This poor organ specificity is undesired for many applications.

Promoters which cause leaf-specific, preferably permanent, expression of genes under their control have not been disclosed.

It would therefore be desirable to find routes to express genes in plants while avoiding the above disadvantages.

It is an object of the present invention to provide means which allow a targeted, organ-specific gene expression in plants. These means should, for example, be suitable for the expression of resistance genes and genes which modify the photosynthesis rate.

BRIEF SUMMARY OF THE INVENTION

We have found that this object is achieved, surprisingly, by providing a new promoter which causes a preferentially permanent, leaf-specific expression, in plants, of an encoding nucleotide sequence under the control of said promoter independently of induction factors.

BRIEF DESCRIPTION OF THE SEVERAL VIEWS OF THE DRAWING(S)

The invention is now illustrated in greater detail with reference to the figures which follow.

FIG. 1 shows (A) a schematic representation of the BamHI fragment of potato clone FBP-1 which has been cloned into vector pUC19 and comprises approx. 7100 bp. The cytosolic FBPase(cy-FBPase) promoter region is shown in black; (B) the construction scheme of plasmid FBP:p-Blue;

FIG. 2 shows the nucleotide sequence of the potato cy-FBPase promoter. The region which is complementary to the 3' end of the 5' subfragment, of the cy-FBPase, used for the Southern hybridization is underlined; two palindromic sequence portions are underlined by a dotted line; the 5'-terminal sequence "GGATC" was added to the genomic DNA to produce a BamHI cleavage site;

Figure 5:
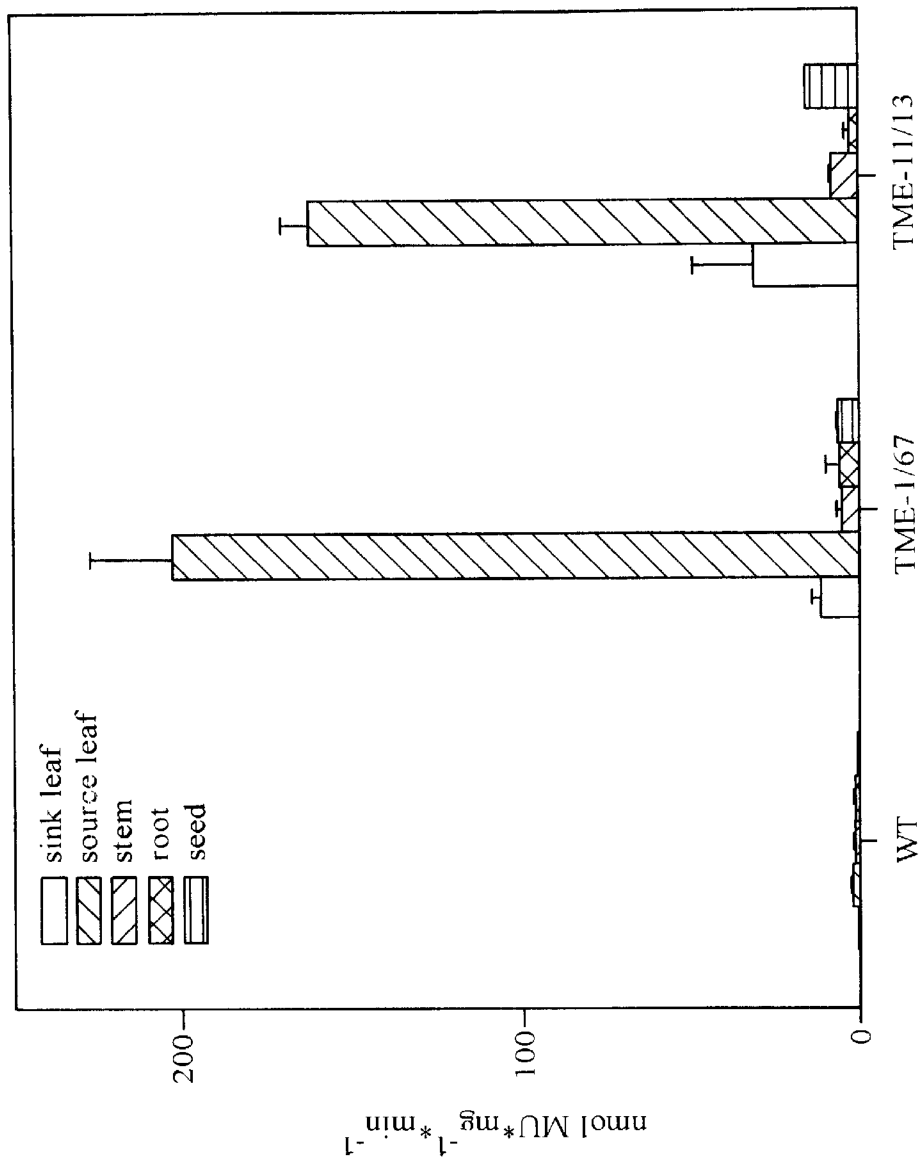
Figure 7:
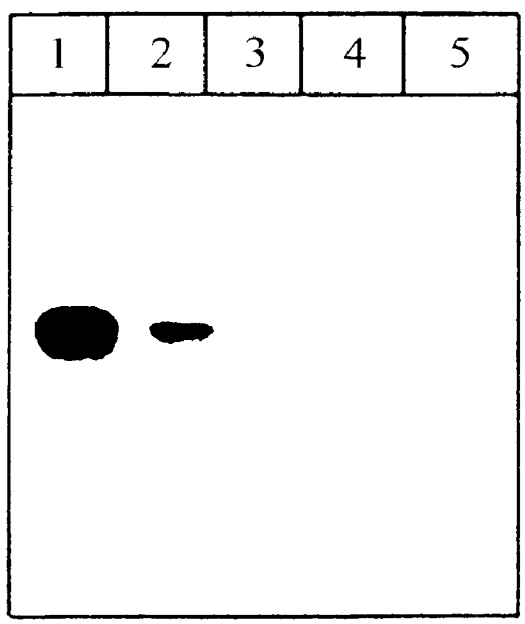
Figure 8:
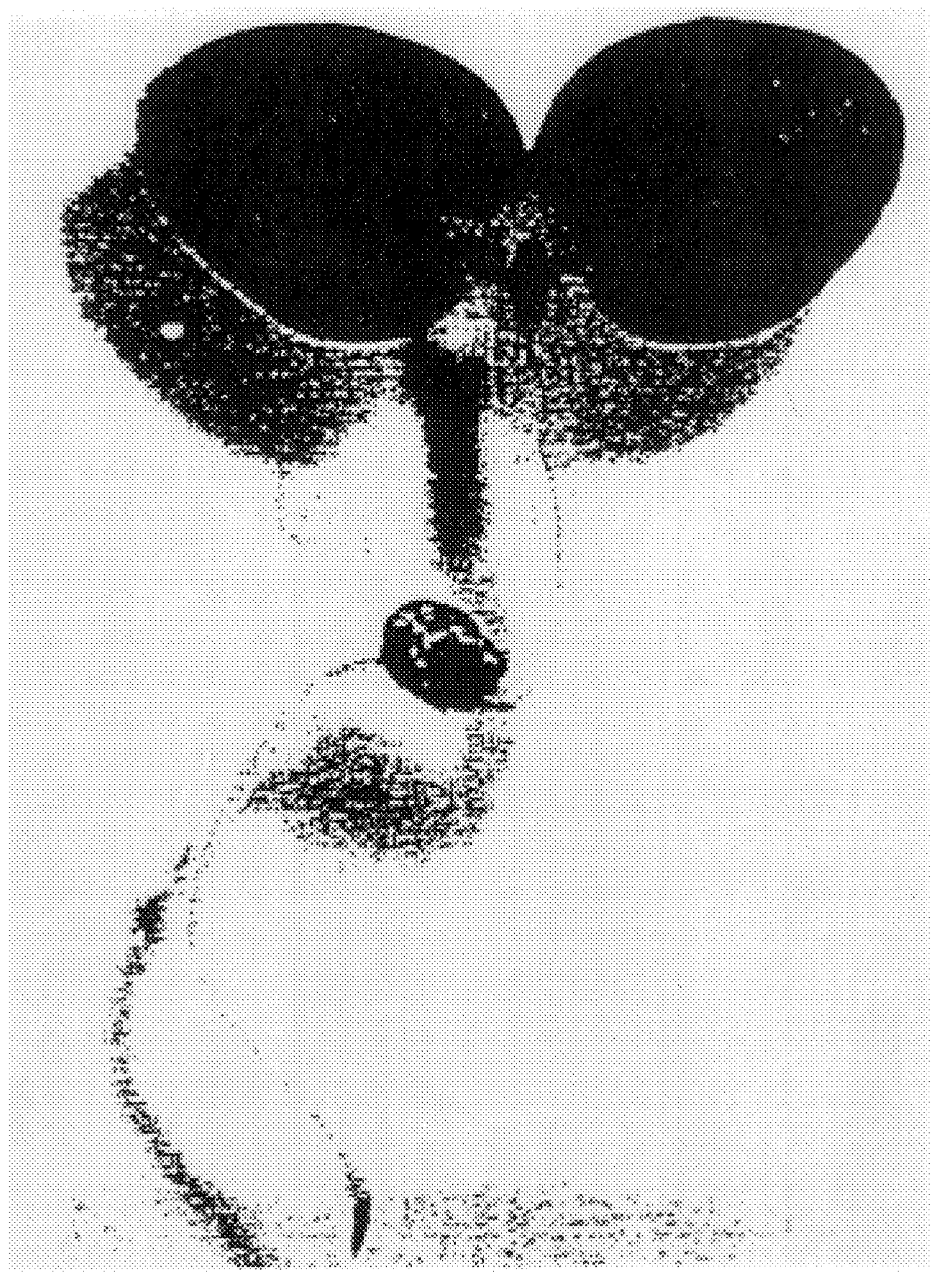
Figure 9:
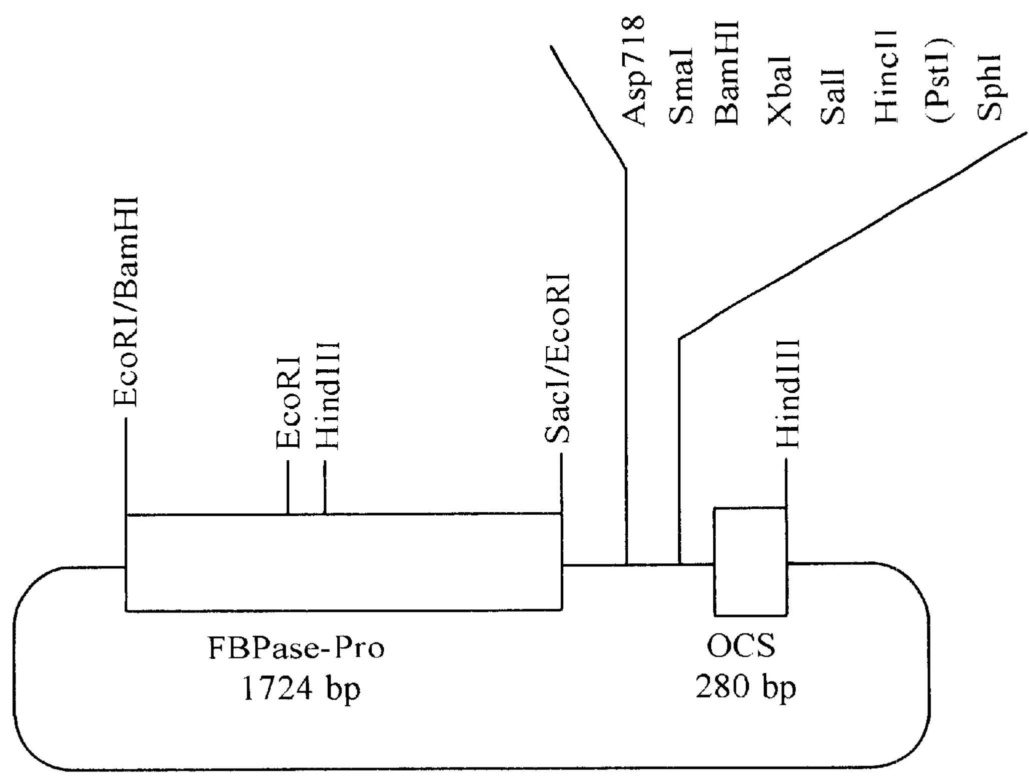

FIG. 5 shows a bar chart which confirms the cy-FBPase-promoter-controlled, leaf-specific GUS activity in transformed tobacco plants. "TME-1/67" refers to the results obtained with vector FBP:GUS. "TME-11/13" refers to the results obtained with vector FBP:GUS (DEL). "WT" shows the results obtained for the wild type. The data shown are the amount of 4-methylumbelliferone formed, per milligram of protein per minute;

FIG. 6 shows the histochemical detection of GUS activity in various tissues of the tobacco leaf in a transgenic plant. (A) Cross-section of the central vascular bundle of the source leaf, (B) epidermis, (C) cross-section of the petiole, (D) cross-section of the mesophyll of a source leaf. The sections were fixed for 20 minutes in 3% strength paraformaldehyde solution and subsequently incubated overnight in X-Gluc solution. Then, the chlorophyll was removed using 70% ethanol;

FIG. 7 shows a Northern blot which illustrates the uniform leaf-specific GUS expression in transgenic tobacco plants, mediated by the potato cy-FBPase promoter;

FIG. 8 shows a histochemical proof of the β-glucuronidase(GUS) activity in tobacco seedlings;

FIG. 9 shows a schematic representation of plasmid pBin-FBP with the potato cy-FBPase promoter which comprises 1724 bp and the octopine synthase terminator which comprises 280 bp, inserted into vector pBin 19, and FIG. 10 shows a cDNA probe of the potato cy-FBPase gene (EMBL No.: X76946).

DETAILED DESCRIPTION OF THE INVENTION

The term "gene" or "encoding (nucleotide) sequence" denotes for the purposes of the present invention a nucleotide sequence which encodes a specific, if appropriate hereditary, structure, for example at least one protein, at least one ribozyme or at least one antisense RNA; or function, for example resistance; or an altered profile of the plant constituents, such as oils, lipids, enzymes, proteins, biopolymers, so that, for example, the nutritional value, the yield or the industrial usability of the plant is improved.

A "promoter" refers, in accordance with the invention, to a nucleotide sequence region which governs transcription of a gene, or the synthesis of the corresponding mRNA. The promoter comprises a sequence which is positioned 5'-upstream of the transcription start. It comprises, as essential sequence element, at least the so-called "TATA" box. Other regulatory elements, such as the "CAAT" box or a GC box, may also be present. In addition, it may be necessary for the promoter sequence according to the invention to have, in addition to the abovementioned sequence section, a sequence positioned 3'-downstream of the transcription start, for example a leader sequence or part thereof, so as to show, or fully exert, the desired promoter activity and/or promoter specificity.

"Resistance" for the purposes of the present invention denotes the artificially induced resistance or tolerance of the transgenic plants to herbicides and/or pathogens, for example fungi, viruses or insects, to specific external conditions, such as high concentrations of ozone, sulfur dioxide, nitric oxides or other exogenous pollutants, and to high and low temperatures, drought or UV light.

A "modification of the photosynthesis rate of a plant" embraces the reduction in, and, in particular, increase of, the photosynthetic activity of the transformed plants. This may be effected for example by expressing genes which improve the light utilization of the plant in a targeted manner, increase the reaction rate of individual, rate-determining metabolic steps, or have an effect on the exchange of substances with the environment.

"Leaf specificity" for the purposes of the present invention means that a foreign gene which is under the control of a promoter according to the invention is expressed in the entire leaf organ or in specific leaf tissues preferably in the mesophyll (for example palisade parenchyma), but not in the shoot or in other parts of the plant such as, in particular, the roots. In particular, "leaf specificity" for the purposes of the present invention also exists when the promoter according to the invention favors the expression of a foreign gene in the leaf, preferably in the mesophyll of leaves, in particular of source leaves, in comparison with other plant organs, such as stem, non-germinating tubers, fruits or seeds of the plant, and causes, in leaves, a significantly higher expression, for example at least approximately 5 to 10 times, such as 10 to 100 times higher.

"Source leaves" of a plant are the old leaves of a plant which fix an excess of carbon by means of photosynthesis and thus export bound carbon into other plant organs, for example the younger "sink" leaves.

"Permanent" expression for the purposes of the present invention denotes an expression, of the gene under the control of the promoter according to the invention, which is essentially independent of exogenously applied chemical induction signals and which persists over one or more plant generations.

Firstly, the present invention relates to promoters which cause a preferentially permanent, leaf-specific expression, in plants, of encoding nucleotide sequences under the control of said promoters.

The primary site of action of herbicides and of a large number of pathogens is the leaf tissue, so that a leaf-specific expression of the resistance genes in question would provide sufficient protection. Since photosynthesis equally proceeds in the leaf tissue, the modification and, in particular, improvement of the photosynthetic performance would require the leaf-specific expression of one or more genes which have an effect on the photosynthesis rate.

The promoters according to the invention now have the surprising advantage of being able to express resistance genes specifically at the actual site of action within the plant. On the other hand, it is possible, for the first time, to influence the photosynthesis rate in a targeted manner by using the promoters according to the invention. As surprisingly demonstrated by the test results, preferred promoters make possible, for the first time, specific localization and expression of a foreign gene in the mesophyll of leaves, in particular of source leaves, while no activity can be found in parenchymatic tissue and also in xylem, phloem and others.

A promoter according to the invention can be provided by isolating and characterizing promoters of leaf-specifically and preferentially permanently expressed genes. Preferred promoters are those which correspond essentially to the promoters of the cytosolic fructose-1,6-bisphosphatase genes (cy-FBPase genes) from leaf-specific mesophyll cells of plants. Especially preferred according to the invention are cy-FBPase promoters which have been isolated from leaf-specific mesophyll cells of plants of the genus Solanum (potatoes), and functional equivalents thereof. A preferred embodiment relates to a nucleotide sequence with the desired promoter activity which is isolated from *Solanum tuberosum* var. Desiree, or functional equivalents thereof. Particularly preferred is a promoter with a nucleotide sequence, chosen from SEQ ID NO: 1 to 5, or functional equivalents of these sequences.

The transcription start point in the preferred nucleotide sequence in accordance with SEQ ID NO: 1 was determined with the aid of "primer extension" using an ALF (automatic laser fluorescence DNA sequencer (Pharmacia)). To this end, a 5'-fluorescence-labeled oligonucleotide was constructed which is complementary to a 21 bp region in the promoter from +1577 to +1599 (SEQ ID NO: 1). With the aid of this primer, total RNA from source leaves was transcribed into single-stranded cDNA. The RNA which was not recognized by the primer and the RNA portions of the cDNA/RNA hybrids were subsequently digested. The cDNA was then analyzed on the ALF simultaneously with the promoter-DNA sequenced with the same primer. It was possible to identify the transcription start point by comparing the signals in the sequence gel. According to this, sequence SEQ ID NO: 1 comprises 1428 bp promoter region (SEQ ID NO: 4) and 292 bp 5'-untranslated region of the cyt FBPase. A TATA box sequence ("TTATAAA") was found 30 bp upstream of the start point, and a CAAT box ("ATCATCCAAACAT") 141 bp upstream of the start point. In addition, several inverted and direct sequence repeats were found which show no homology to sequence repeats which have been found in other promoters.

The direct and inverted sequence repeats which have been with a length of at least 10 bp, are listed in the tables which follow.

Direct Sequence Repeats

| Fragment starting at base | Repeat starting at base | Size | Repeat sequence 5' 3' |
|---|---|---|---|
| 225 | 1316 | 10 | AAGGATATTT |
| 269 | 1686 | 11 | TCTTTTTTTTT |
| 825 | 1016 | 12 | TCAAAAGTTATG |
| 1039 | 1493 | 13 | ATATGTGACGTGG |
| 1083 | 1535 | 11 | ATAGAAACAAA |
| 1085 | 1411 | 10 | AGAAACAAAA |
| 1172 | 1608 | 12 | GTGCCAACCACT |
| 1203 | 1639 | 13 | CTCTTTCCACGTG |

Inverted Sequence Repeats

| Fragment starting at base | Repeat starting at base | Size | Repeat sequence 5' 3' |
|---|---|---|---|
| 99 | 293 | 10 | CAAACATTTT |
| 275 | 275 | 10 | TTTTTAAAAA |
| 313 | 1132 | 10 | AACTTCTGTT |
| 535 | 535 | 10 | TGCATATGCA |
| 835 | 835 | 10 | TGCAGCTGCA |
| 1269 | 1370 | 11 | TGTATATCAAA |
| 1293 | 1359 | 10 | TCATCCAAAC |
| 1401 | 1401 | 10 | TTTTATAAAA |
| 1658 | 1658 | 12 | TCTGACGTCAGA |

The position data are based in each case on the numbering of the nucleotide residues in accordance with SEQ ID NO:2.

The above list contains, in particular, two virtually identical palindromic sequence sections of 10 bp which contain in each case twice the motif TGCA. This motif exists in the complementary strand as ACGT, a box which has been identified by various workers as a regulatory sequence (for example Guliano et al., (1998), Proc. Acad. Natl. Sci. USA, 85, 7089–7093) and as a binding site for DNA-binding leucin zipper proteins (for example Armstrong et al., (1992), Plant Cell, 4, 525–537). The binding of leucin zipper proteins is probably not affected by the orientation of the motif. These sequences are marked in FIG. 2 by underlining with a dotted line. The effect of the above part-sequences on the promoter activity and/or promoter specificity according to the invention can be tested by those skilled in the art, for example with the aid of customary deletion experiments.

A further preferred embodiment of the invention relates to a 5'-shortened promoter sequence (SEQ ID NO: 3). It comprises a 817 bp promoter region (SEQ ID NO: 5) and a 292 bp 5'-untranslated region. Surprisingly, the organ or tissue specificity of the shortened promoter is identical to that of the above-described, longer promoter, but the promoter activity of the shortened promoter is different.

Functionally equivalent promoter sequences are, according to the invention, those sequences which despite differing nucleotide sequence still have the desired functions, ie. promoter activity and tissue or organ specificity. A measure for the promoter activity is, for example, the expression rate determined for a certain marker gene which is under the regulatory control of the promoter according to the invention. Examples of suitable marker genes are the β-glucuronidase (GUS) gene from *E. coli* or the green fluorescence protein (GFP) gene (Baulcombe et al., (1993), Plant J., 7 (6), 1045–1053)). The organ or tissue specificity can be determined readily by comparing the expression rates, for the above marker genes, determined in individual tissues or organs of the plant. Functional equivalents for the purposes of the present invention embrace naturally occurring variants of the sequences described herein as well as artificial nucleotide sequences, for example those obtained by chemical synthesis and adapted to the codon usage of a plant.

Functional equivalents are to be understood as meaning, in particular, also natural or artificial mutations of an originally isolated promoter sequence which furthermore show the desired function. Mutations embrace substitutions, additions, deletions, exchanges or insertions of one or more nucleotide radicals. Thus, the present invention also embraces for example those nucleotide sequences which are obtained by modifying the nucleotide sequence in accordance with SEQ ID NO:1 to 5. The aim of such a modification can be, for example, a further limitation of the promoter sequence contained therein, or else, for example, the insertion of further restriction enzyme cleavage sites.

Functional equivalents are also those promoter variants whose promoter function is attenuated or more pronounced in comparison with the wild type.

If appropriate, leaf-specifically expressed genes must first be identified by experiments prior to isolation of the promoter sequence, for example by subtractive hybridization (for example as described by R. A. Meyers, Molecular Biology and Biotechnology (1995), VCH, pp. 698–699). Next, a genome library can be established from leaves of the donor organism using known processes, for example by isolating the total DNA, subsequent partial digestion, packaging of fragments of defined size in bacteriophages, infection of bacteria with the recombinant bacteriophages and subsequent amplification of the genome library. The phages containing the genomic DNA can then be transferred for example onto nylon filters and hybridized with a radiolabeled cDNA of the previously identified leaf-specific gene. Hybridizing phage DNAs can be visualized by autoradiography and then individualized. To isolate the phage DNA, it is possible to start from one individual plaque and to inoculate and incubate lytic agar plates and to obtain the DNA in a manner known per se, for example by phenol/chloroform extraction followed by precipitation with ethanol. The fragment lengths of the promoter regions of the genomic clones which have been isolated can now be determined for example by Southern hybridizations using a 5'-cDNA probe of the leaf-specifically expressed gene following various restriction cleavages. Now, a promoter region can be cloned into a suitable vector, propagated, for example in *E. coli*, and the complete nucleotide sequence of the promoter can be determined by sequencing. Suitable cloning vectors are, inter alia, pBR332, pUC series, M13mp series and pACYC184.

Expediently, the promoter may now be linked operatively with a suitable gene in an expression cassette so that the promoter is capable of controlling transcription of the gene fused to it. Operative linkage is to be understood as meaning the sequential arrangement of promoter, encoding sequence, terminator and, if appropriate, other regulative elements, allowing each of the abovementioned elements to fulfil its function in gene expression as intended.

The present invention furthermore relates to such an expression cassette. The invention furthermore relates to recombinant vectors, for example plasmids or viruses, which comprise at least one expression cassette according to the invention.

In principle, the nucleotide sequences downstream of the promoter sequence of the expression cassette may contain all open reading frames which are possible for any peptide, and one or more introns. Examples which may be mentioned are: sequences for enzymes; sequences which are complementary to a) a genome sequence, it being possible for the genome sequence to be an open reading frame; b) an intron; c) a non-encoding leader sequence; d) any sequence which—when integrated into the genome in a complementary fashion—inhibits transcription, mRNA-processing (for example splicing) or translation.

The nucleotide sequence inserted can be produced synthetically or obtained naturally or comprise a mixture of synthetic and natural DNA components. In general, synthetic nucleotide sequences are produced with codons preferred by plants. These codons preferred by plants can be determined from codons with the highest frequency of protein and which are expressed in the most interesting plant species. When preparing an expression cassette, various DNA fragments can be manipulated in order to obtain a nucleotide sequence which expediently reads in the correct direction and which is provided with a correct reading frame. To link the DNA fragments to each other, adaptors or linkers may be added to the fragments.

The promoter regions according to the invention and the terminator regions should expediently be provided in the direction of transcription with a linker or polylinker comprising one or more restriction sites for inserting this sequence. As a rule, the linker has 1 to 10, in most cases 1 to 8, preferably 2 to 6 restriction sites. In general, the linker has a size of less than 100 bp, frequently less than 60 bp, but at least 5 bp, inside the regulatory regions. The promoter according to the invention can be native or homologous to the host plant, but also foreign or heterologous thereto. The expression cassette according to the invention comprises, in the 5'-3' direction of transcription, the promoter according to the invention, any sequence and a region for transcriptional termination. Various termination regions can be exchanged for each other as desired.

It is furthermore possible to employ manipulations which provide suitable restriction cleavage sites or which remove excess DNA or restriction cleavage sites. Where insertions, deletions or substitutions, for example transitions and transversions, are suitable, it is possible to use in-vitro mutagenesis, "primer repair", restriction or ligation. In the case of suitable manipulations, for example restriction, "chewing back" or filling up overlapping sections for blunt ends, it is possible to provide complementary ends of the fragments for ligation.

Especially suitable encoding nucleotide sequences are tolerance- or resistance-inducing genes, genes which increase the photosynthetic performance of the plant, or marker genes such as the β-glucuronidase gene (GUS) from *Escherichia coli*. Examples of suitable tolerance genes are those which increase the tolerance of a plant to temperature, drought, UV or environmental pollutants. Examples of suitable resistance genes are the bar gene from *Streptomyces hygroscopicus*, which mediates resistance to the total herbicide phosphinothricin, chitinase genes which mediate tolerance to fungal infections, and ribozyme genes whose RNA transcripts are capable of recognizing and cleaving viral RNA with high specificity. These and other resistance genes are known from Transgenic Plants and Crop Improvement, in Transgenic Plants, Vol. 1, Engineering and Utilization, edited by S-d Kung and R. Wu, Academic Press, 1993, Part III, pp. 243–372; and from R. H. Symons (1992), Small catalytic RNAs, Ann. Rev. Biochem. 61, 641–671. Examples of suitable genes for increasing the photosynthetic performance are the genes which encode sucrose phosphate synthase (SPS) or fructose-1,6-bisphosphatase (FBPase).

The fused construct can now be transferred into plant genomes by various known processes. Examples of suitable processes are protoplast transformation by polyethylene glycol-induced DNA uptake, electroporation, sonication or microinjection, and the transformation of intact cells or tissue by micro- or macroinjection into tissue or embryos, tissue electroporation, incubation of dry embryos in DNA-containing solution, biolistic gene transfer and, especially preferably, Agrobacterium transformation. The abovementioned processes are described, for example, in B. Jenes et al., Techniques for Gene Transfer; in Transgenic Plants, Vol. 1, Engineering and Utilization, edited by S-d Kung and R. Wu, Academic Press, 1993, pp. 128–143 and in Potrykus (1991) Annu. Rev. Plant Physiol. Plant Molec. Biol. 42, 205–225. The fused construct is preferably cloned into a vector which is suitable for transforming *Agrobacterium tumefaciens*, for example pBin19 (Bevan et al. (1980) Nucl. Acids Res. 12, 8711). The present invention furthermore relates to such vectors and to microorganisms transformed with them, in particular Agrobacterium.

Then, agrobacteria which have been transformed with a vector according to the invention can be used in a known manner for the transformation of plants, in particular crop plants such as cereals, maize, soya, rice, cotton, sugarbeet, canola, sunflower, flax, potato, tobacco, tomato, oilseed rape, alfalfa, lettuce and the various tree, nut and grape vine species, for example by bathing scarified leaves or leaf sections in an agrobacteria solution and subsequently culturing them in suitable media.

The present invention furthermore relates to the use of vectors according to the invention for the transformation of plants. The transformation of plants by agrobacteria is known, inter alia, from F. F. White, Vectors for Gene Transfer in Higher Plants; in Transgenic Plants, Vol. 1, Engineering and Utilization, edited by S-d Kung and R. Wu, Academic Press, 1993, pp. 15–38 and from S. B. Gelvin, Molecular Genetics of T-DNA Transfer from Agrobacterium to Plants, also in Transgenic Plants, pp. 49–78. Transgenic plants which express the gene which is under the control of the promoter introduced and fused thereto, in a leaf-specific manner, can be regenerated from the transformed cells of the scarified leaves or leaf sections in a known manner. The present invention furthermore relates to such transgenic plants, propagation material thereof and to plant cells, plant tissue or parts of plants.

The cloning steps carried out for the purposes of the present invention, for example restriction cleavage, agarose gel electrophoresis, purification of DNA fragments, transfer of nucleic acids to nitrocellulose and nylon membranes, linking DNA fragments, transformation of *E. coli* cells, growing bacteria, multiplication of phages and sequence analysis of recombinant DNA were carried out as described by Sambrook et al. (1989) Cold Spring Harbor Laboratory Press; ISBN 0-87969-309-6.

The invention is illustrated by the examples which now follow, but not limited thereto:

The bacterial strains used hereinbelow (*E. coli*, XL-1 Blue and P2 392) were obtained from Stratagene. The *Agrobacterium tumefaciens* strain employed for the transformation of plants (C58C1 with the plasmid pGV 3850kan) was described by Debleare et al. (1985, Nucl. Acid Res. 13, 4777). The cloning vectors used were pUC19 (Yanish-Perron (1985) Gene 33, 103–119), pBlueScript SK (Stratagene), pBin19 (Bevan (1984) Nucl. Acids Res. 12, 8711–8720) and pBI101 (Jefferson et al. (1987) EMBO J. 6, 3901–3907).

*Solanum tuberosum* L variety Desirée was obtained from Vereinigte Saatzuchten eG Ebstorf.

*Nicotiana tabacum* L Samsun NN was obtained from Vereinigte Saatzuchten eG Ebstorf.

EXAMPLE 1

Isolation of a Leaf-specific Promoter

1. Isolation of a Leaf-specifically Expressed Gene 1.1. Probe used

A cDNA probe of the potato cy-FBPase gene, produced using reverse transcriptase (EMBL No.: X76946) was used for the experiments described hereinbelow. The cDNA probe (FIG. 10) embraced 1487 nucleotides. The region which encodes the structural gene (FBPase) embraces nucleotides 199 to 1218.

1.2.Establishing a Genome Library

To establish a genome library from potato (*Solanum tuberosum* var. Desiree), total DNA from potato leaves was isolated by the method described by Rogers et al. ((1985) Plant Mol. Biol. 5, pp. 69–76). 300 μg of the DNA were subsequently subjected to partial digestion with the restriction enzyme Sau3A, and the fragments between 12 and 20 kb were isolated by means of sucrose gradient centrifugation, dialyzed and concentrated by shaking with butanol.

The DNA was ligated into BamHI-digested EMBL3 arms obtained from Stratagene (11099 North Torrey Pines Road, La Jolla, Calif. 92037, USA) following the manufacturer's information and subsequently packaged in vitro (Gigapack II Gold packaging extracts, Stratagene, following the manufacturer's information). *E. coli* bacteria of strain P2 392 (Stratagene) were infected with the recombinant lambda phages, the titer of the library was determined, and the library was subsequently amplified.

1.3.Screening of the Genome Library, and Isolation of the cy-FBPase Gene

To isolate a genome clone comprising the cy-FBPase gene, $3\times10^5$ phages were plated. After the phages had been transferred to nylon filters (Hybond N, Amersham Buchler), the filters were baked for 2 hours at 80° C. for fixing. They were subsequently prehybridized in Hypo-Hybond buffer at 42° C.

1 l of Hypo-Hybond buffer contains:

250 ml of 1M sodium phosphate buffer pH 7.2

50 ml of 5M NaCl 2 ml of 0.5M EDTA pH 8.0

2 ml of sonicated herring sperm DNA, 1 mg/l 400 ml of formamide 50 g of PEG 6000

70 g of SDS 200 ml of water

The potato cy-FBPase sample which had been radiolabeled with High-Prime (Boehringer Mannheim) was first denatured for 5 minutes at 95° C. and then placed in the prehybridization solution. The filters were hybridized overnight at 42° C. After the radioactive hybridization solution had been stripped off, the filters were washed for 20 minutes at 42° C. in 2× SSC (an NaCl/sodium citrate buffer), 0.1% SDS. The filters were subsequently washed again for 20 minutes at the same temperature using 1× SSC, 0.1% SDS. Then, a film was placed on the filters and exposed overnight at −70° C.

4 hybridizing phage DNAs were visualized by autoradiography and individualized. Starting from in each case one individual plaque, in each case one lytic agar plate was inoculated, incubated overnight at 37° C., and the phages were rinsed off the next day with 10 ml of phage buffer (SM). The phage supernatant was subsequently treated with chloroform and the bacteria were centrifuged off. The supernatant was treated with in each case one spatula-tip of DNase and RNase and the mixtures were incubated for 30 minutes at 37° C. After 100 μl of 0.5 M EDTA and 200 μl of 10% strength SDS solution had been added, the batch was incubated for a further 20 minutes at 65° C. Then, 4.5 ml of 3M potassium acetate solution pH 4.8 were added and the batch was mixed and centrifuged. The supernatant was subsequently extracted by shaking with phenol:chloroform:isoamyl alcohol (volumetric ratio 25:24:1). After extraction, the DNA was precipitated from the supernatant by adding two volumes of ethanol, and the resulting sediment was dissolved in 600 μl of TE-RNase.

2. Localization of the Promoter

Figure 1A:
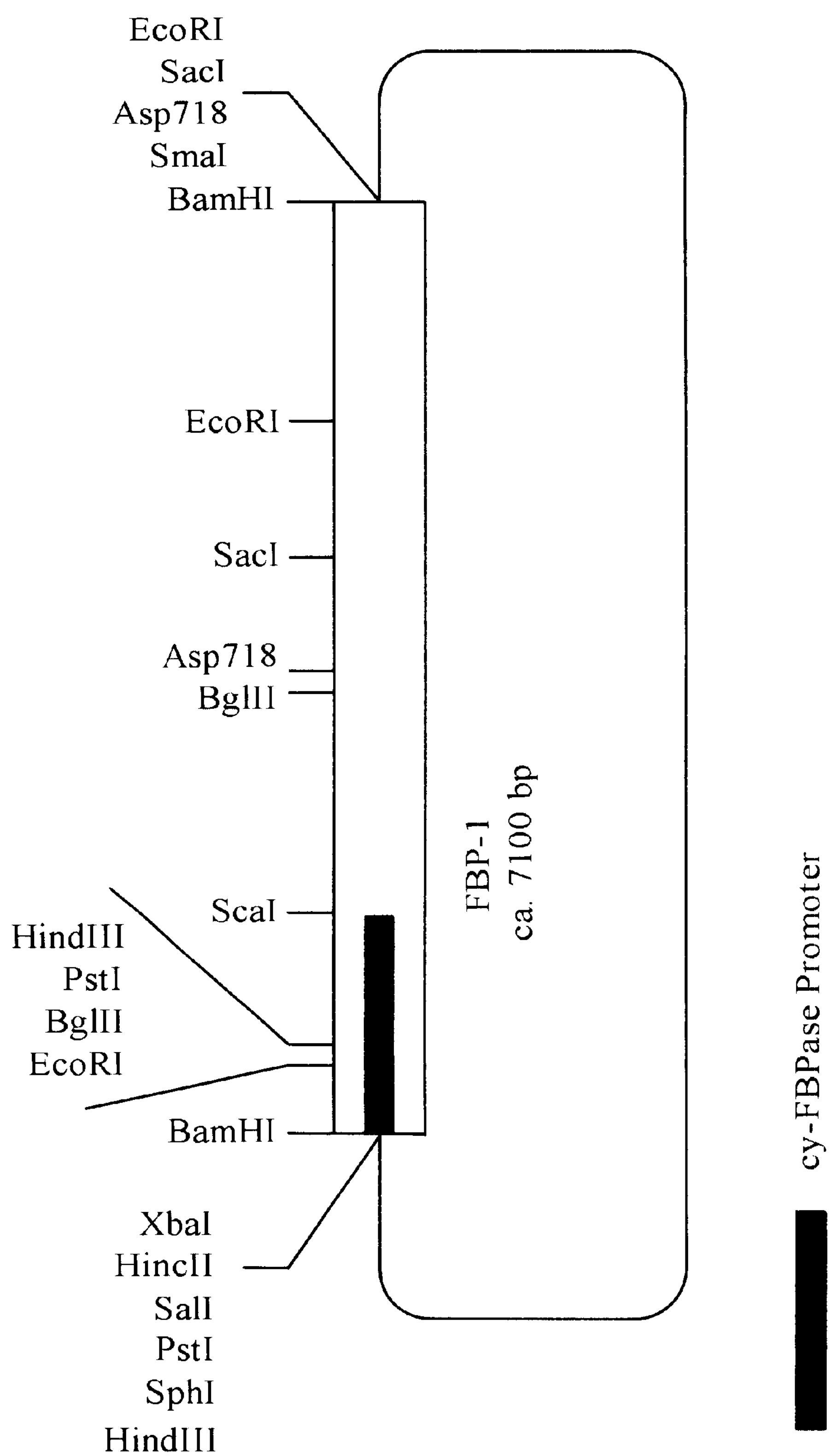
Figure 1B:
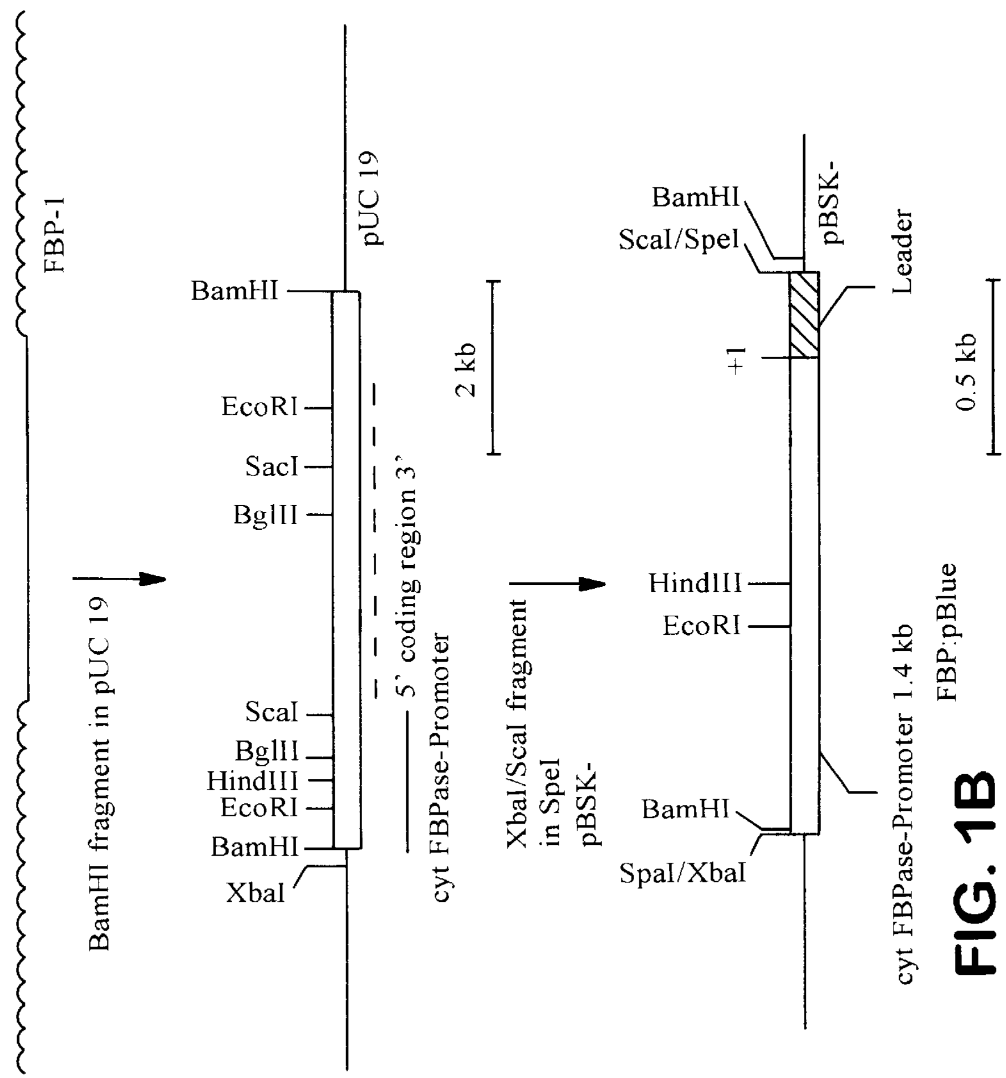

The fragment lengths of the promoter regions of the 4 clones which had been isolated were determined by Southern hybridizations with a 5'-cDNA sample following various restriction cleavages. Clone FBP-1 was selected for further analyses. An approximately 7100 b BamHI fragment of clone FBP-1 was cloned into the BamHI cleavage site of vector pUC19 for further characterization. Sequencing, Southern hybridization and restriction analysis allowed the promoter region to be restricted to a 1724 base pair fragment (FIG. 1A). The probes used for the Southern hybridization were the 5'-342 bp (HincII/EcoRI) and 3'-216 bp (EcoRI/EcoRV) subfragments of the CDNA of the cy-FBPase. It was known from the sequence of the cDNA of the cytosolic FBPase that the restriction enzyme ScaI cleaves in the non-encoding 5' region of the CDNA. A single ScaI cleavage site was found in the genomic clone FBP-1. Sequence information on the genomic clone made it possible to demonstrate that this was the cleavage site which corresponded to the CDNA. It was used to remove the promoter region from the encoding region. To this end, the promoter region XbaI/ScaI was excised from the clone FBP-1, the ends were filled up and ligated into the vector pBlueScript-SK (pBSK-), which had previously been SpeI-cleaved and filled up (termed FBP:pBlue). The preparation of FBP:pBlue is shown diagrammatically in FIG. 1B. The complete DNA sequence as subsequently determined by sequencing (FIG. 2).

EXAMPLE 2

Preparation of a Transformation Vector

1. Preparation of Plasmid FBP:GUS

The expression characteristics of the new promoter were analyzed by marker gene experiments. To this end, the cy-FBPase promoter was fused with the β-glucuronidase gene (GUS) from *E. coli*. The promoter was isolated from plasmid FBP:pBlue as a BamHI fragment and cloned into the BamHI cleavage site of expression vector pBI101 (FIG. 3A) (Jefferson et al., (1987), EMBO J. 6, 3901–3907). The resulting plasmid FBP:GUS (FIG. 3B) was subsequently employed for the transformation of *Agrobacterium tumefaciens*.

2. Preparation of the Deletion Construct FBP:GUS(DEL)

Figure 3A:
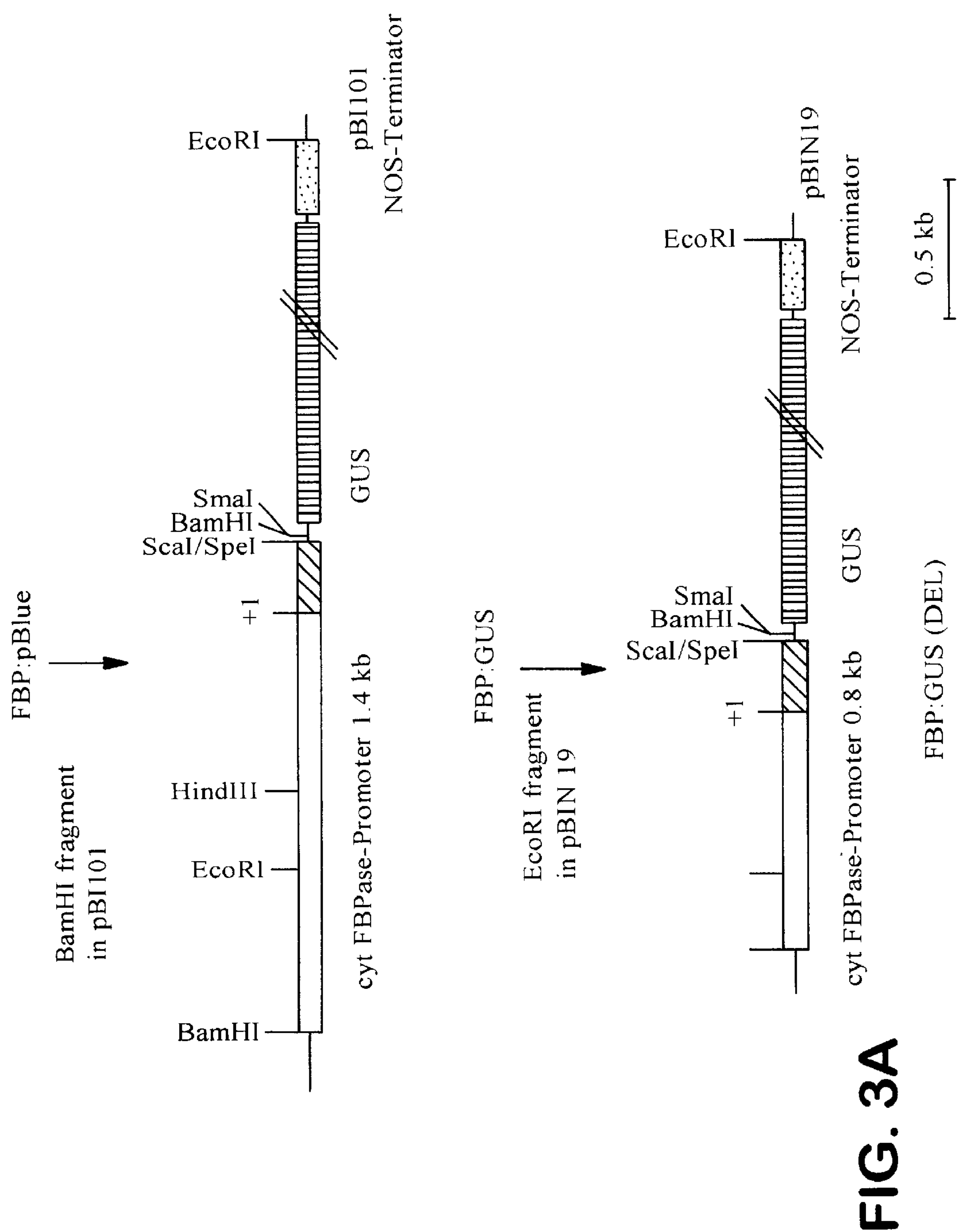
FIG. 3 shows (A) the construction scheme of plasmids FBP:GUS and FBP:GUS (DEL); (B) a schematic representation of plasmid FBP:GUS with the FBPase promoter comprising approx. 1700 bp, the GUS gene comprising approx. 1870 bp and the nopaline synthase terminator comprising approx. 260 bp, inserted into vector pBI 101.
Figure 3B:
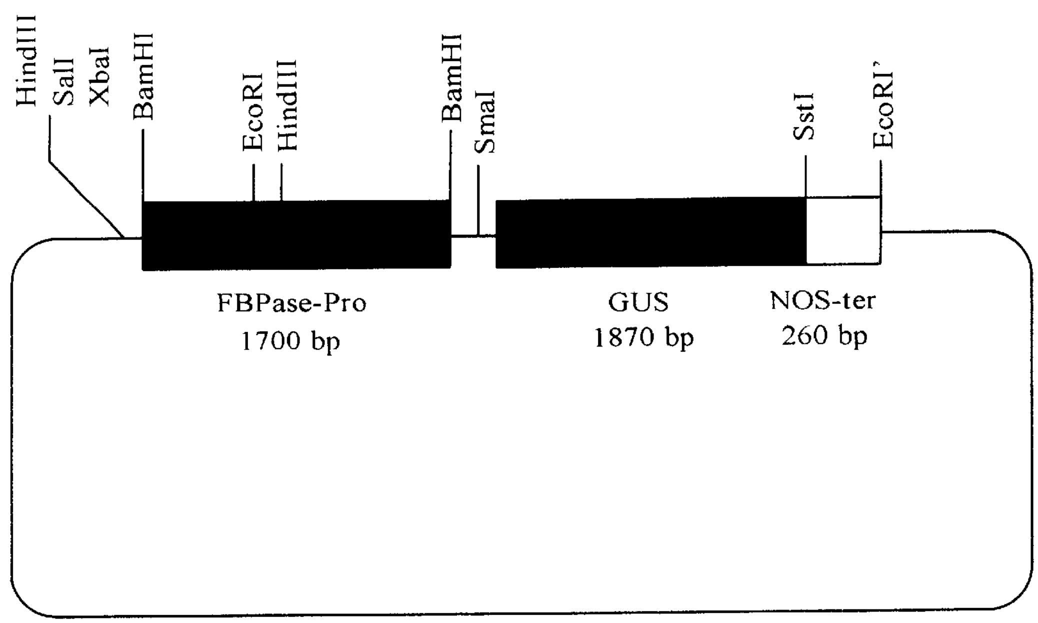

A deletion construct was prepared which comprises approximately 1.1 kb of the promoter sequence. To this end, a fragment comprising the GUS gene, the NOS terminator and 1100 bp of the promoter was excised from FBP:GUS by means of EcoRI digest. This fragment was isolated, purified and ligated into the EcoRI cleavage site of the vector pBin 19 (FIG. 3A). The orientation of the fragment in pBin 19 was checked by cleavage with BamHI. *Agrobacterium tumefaciens* was also transformed with this vector.

EXAMPLE 3

Transformation of *Agrobacterium tumefaciens*

The transformation of *Agrobacterium tumefaciens* was carried out following the method of Höfgen-and Willmitzer (Nucl. Acid Res. (1988) 16, 9877). The agrobacteria were grown in YEB medium (Vervliet et al., J. Gen. Virol. (1975) 26, 33).

EXAMPLE 4

Transformation of the cy-FBPase Promoter in Tobacco and Potato Plants, and Analysis of Expression 1.1 Transformation of Tobacco For the transformation of tobacco plants (*Nicotiana tabacum* L. cv. Samsun NN), 10 ml of an overnight culture of *Agrobacterium tumefaciens* which had been transformed with FBP:GUS or FBP:GUS (DEL) and grown under selection were centrifuged, the supernatant was discarded, and the bacteria were resuspended in the same volume of an antibiotic-free medium. Leaf disks of sterile plants (approximate diameter 1 cm) were bathed in this bacterial solution in a sterile Petri dish. The leaf disks were subsequently placed on MS medium (Murashige and Skoog, Physiol. Plant. (1962) 15, 473) with 2% sucrose and 0.8% Bacto agar in Petri dishes. After incubation in the dark for 2 days at 25° C., they were transferred to MS medium with 100 mg/l kanamycin, 500 mg/l claforan, 1 mg/l benzylaminopurine (BAP), 0.2 mg/l naphthylacetic acid (NAA), 1.6% glucose and 0.8% Bacto agar, and culturing was continued (16 hours light/8 hours dark). Growing shoots were transferred to hormone-free MS medium with 2% sucrose, 250 mg/l claforan and 0.8% Bacto agar.

1.2.Transformation of Potatoes 20 small leaves, scarified with a scalpel, of a sterile potato culture were placed into 10 ml of MS medium with 2% sucrose which contained 50 μl of an FBP:GUS or FBP:GUS (DEL) transformed *Agrobacterium tumefaciens* overnight culture which had been grown under selection. After gentle shaking for 5 minutes, the Petri dishes were incubated at 25° C. in the dark. After two days, the leaves were placed on MS medium with 1.6% glucose, 2 mg/l zeatin ribose, 0.02 mg/l gibberellic acid, 500 mg/l claforan, 50 mg/l kanamycin and 0.8% Bacto agar. After incubation at 25° C. and 3000 Lux for one week, the claforan concentration in the medium was halved. Further culturing was carried out by known methods (Rocha-Sosa et al. (1989) EMBO J. 8, 23–29).

1.3.Expression Analysis of the cy-FBPase Promoter in Transgenic Tobacco and Potato Plants In each case 60 transformed plants from amongst the transformed tobacco and potato plants were regenerated, and the β-glucuronidase activity was determined. β-Glucuronidase was detected as described by Martin et al. (1992) in: The GUS Reporter System as a Tool to Study Plant Gene Expression in: GUS Protocols: Using the GUS Gene as a Reporter of Gene Expression, Academic Press, pp. 23–43. To analyze the expression in greater detail, 40 tobacco plants and 21 potato plants were selected. After the transformed plants had been transferred into the greenhouse, the organ-specific β-glucuronidase expression was determined.

Figure 4:
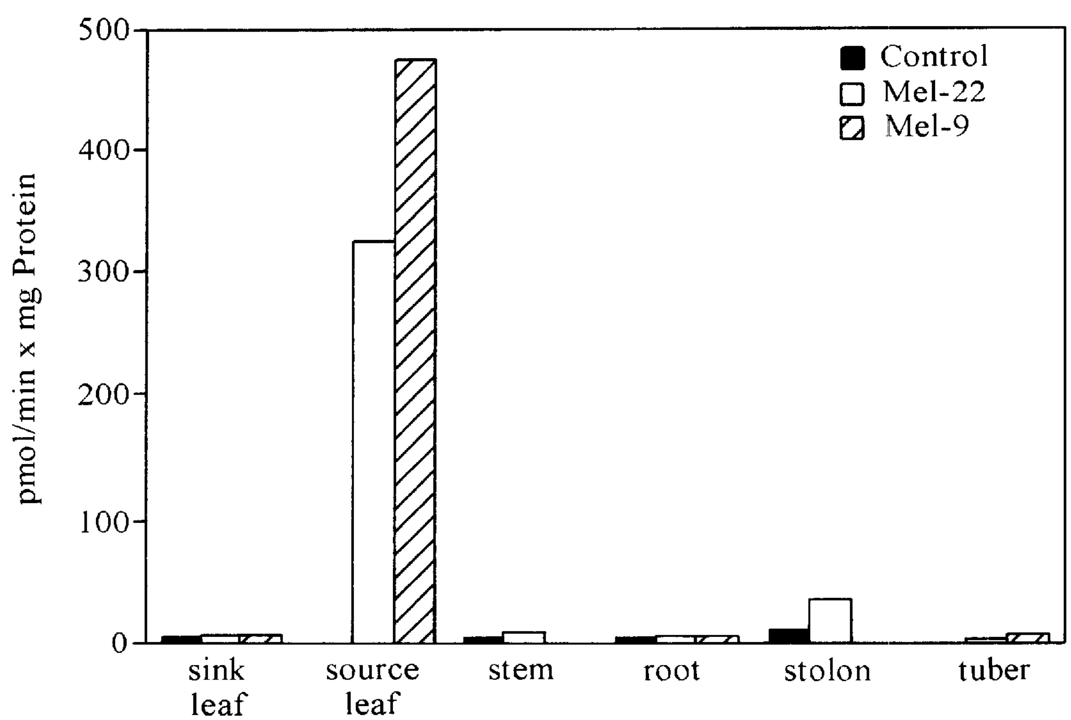
FIG. 4 shows a bar chart which illustrates the cy-FBPase-promoter-controlled leaf-specific GUS activity in transgenic potato plants; it shows the results obtained for two different transformation experiments with FBP:GUS (plant line "Me 1-22" and "Me 1-9"), comparing them with a control experiment ("control")

FIG. 4 shows a comparison of the enzyme activities in different potato tissues. The data show that the promoter mediates leaf-specific expression of the reporter gene.

FIG. 5 shows a comparison of the GUS activity in various organs of the wild type and of transgenic tobacco plants which carry the GUS gene under the control of a variety of promoters according to the invention. TME-1/67 refers to a plant which has been transformed with FBP:GUS. TME-11/13 refers to a plant which has been transformed with FBP:GUS (DEL).

The determination of the GUS activity in the organs sink leaf, source leaf, stem and root of 9-week-old tobacco plants and of seeds revealed that, in both transformation lines, the highest activity is to be found in source leaves and a markedly lower activity in sink leaves. The measurements in sink leaves always differed greatly within one leaf. The activity in stem and root was only marginally above the background activity measured in wild-type tobacco. In these tissues, the promoter is not active. Slightly elevated activity levels were measured in tobacco seeds in comparison with wild-type seeds, even though no mRNA could be detected in the Northern blot. GUS activity in seeds was also found when seed homogenate was incubated in X-Gluc solution. Wild-type seeds show no staining (not shown). It is possible that the promoter is active in the course of seed development and not in the mature seeds themselves. The GUS activity might be explained by stored protein. Depending on the plant, the activity found in the leaves was higher by a factor of approximately 10 to 50 in comparison with seeds.

FIG. 6 illustrates the cell specificity of the construct FBP:GUS according to the invention. Identical histological findings are obtained with the shortened promoter construct FBP:GUS(DEL). To investigate the cell specificity of the cyt FBPase promoter in the leaf in greater detail, leaf cross-sections were prepared of fully unfolded tobacco leaves of 8-week-old plants which had been grown in the greenhouse. The sections were fixed in 3% paraformaldehyde for 20 minutes, stained overnight in X-Gluc (5-bromo-4-chloro-3-indolyl-β-D-glucuronide) solution and the chlorophyll was subsequently removed using 70% ethanol. In addition, the epidermis was removed from the mesophyll and incubated separately to avoid contamination with dibromodichloro-indigo, which had been released into the staining solution by damaged mesophyll cells.

Figure 6A:
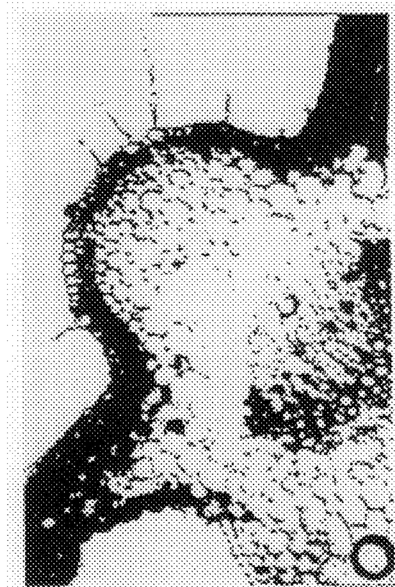
Figure 6C:
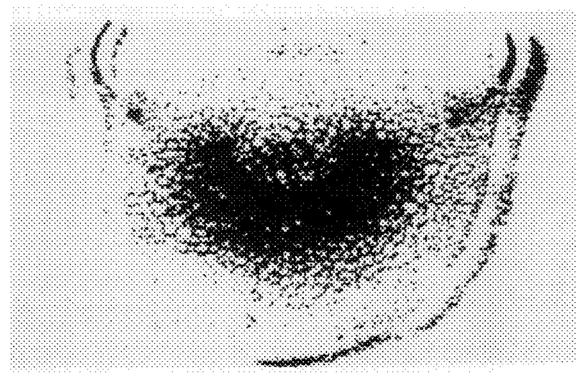
Figure 6B:
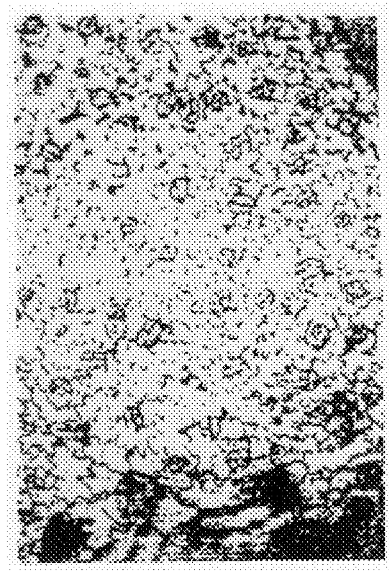
Figure 6D:
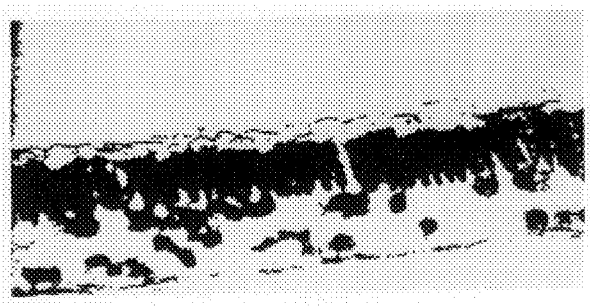

FIG. 6(A) shows a cross-section through the central vascular bundle of a source leaf. It can be seen clearly that, in the central vascular bundle, only the mesophyll cells were stained on the upper side. The parenchymatic tissue and also xylem, phloem and other tissues localized here were not stained. Some of the epidermis cells seem to have been stained. This is probably not an activity in the cells, since the epidermis incubated in isolation shows no GUS activity in trichomes, stomata and epidermal cells (B). Staining of the epidermal cells (A) might be attributed to contamination from the excised mesophyll cells, or to the fact that the sections contained several layers and mesophyll cells located behind the epidermal cells were seen through them. No blue staining was observed in the petiole (C). In the mesophyll cross-section, very strong expression was found in the palisade parenchyma and a slightly less pronounced expression in the spongy parenchyma (D).

To investigate the expression in greater detail, the total RNA was isolated from different organs of tobacco plants (transformed with FBP:GUS), and GUS-specific transcripts were detected by means of Northern analyses (FIG. 7). The isolation was carried out as described by Logemann et al. (Anal. Biochem. (1987) 163,21). For the analysis, in each case 20 to 40 μg of RNA were separated in a 1.5% agarose gel comprising formaldehyde. After electrophoretic separation of the RNA molecules, the RNA was transferred to a nylon membrane by means of capillary transfer. The detection of specific transcripts was carried out as described by Amasino (Anal. Biochem. (1986) 152, 304). The cDNA fragments employed as probe were radiolabeled with a Random Primed DNA Labeling Kit (Boehringer, Mannheim). GUS-specific transcripts were only detected in sink and source leaves, while no positive signal was identified in stalks, roots and seeds. A comparison of the β-glucuronidase activity obtained in sink and source leaves demonstrates that the activity is much higher in source leaves. Histochemical analyses of seedlings revealed that uniform leaf-specific expression is guaranteed even in early developmental stages of tobacco plants (FIG. 8).

EXAMPLE 5

Construction of the Vector pBin-FBP

The promoter fragment was excised from pUC19 using BamHI/SacI; the ends were filled up with T4-DNA-polymerase. The fragment was subsequently separated from vector pUC19 by electrophoresis on a 1% TAE agarose gel and purified with glass milk (BIO 101.1070 Joshua Way, Vista, Calif. 92083, USA). It was then ligated into a pBin19 derivative which had been cleaved with EcoRI and treated with Klenow enzyme. This derivative thus comprised an expression cassette embracing the cy-FBPase promoter and the terminator sequence of octopine synthase from *Agrobacterium tumefaciens* (FIG. 9).

We claim:

1. A method of isolating a mesophyll-specific promoter sequence of a cytosolic fructose-1,6-biphosphatase from potato plants which comprises (a) hybridizing the genome library of a potato plant with cyFBPase cDNA (SEQ ID NO:4), (b) isolating positive clones, and (c) testing the isolated clones for promoter activity.

* * * * *

```
                         SEQUENCE LISTING


(1) GENERAL INFORMATION:

   (iii) NUMBER OF SEQUENCES: 5


(2) INFORMATION FOR SEQ ID NO: 1:

     (i) SEQUENCE CHARACTERISTICS:
          (A) LENGTH: 1720 base pairs
          (B) TYPE: nucleic acid
          (C) STRANDEDNESS: double
          (D) TOPOLOGY: linear

    (ii) MOLECULE TYPE: DNA (genomic)

   (iii) HYPOTHETICAL: NO

    (iv) ANTI-SENSE: NO

    (vi) ORIGINAL SOURCE:
          (A) ORGANISM: Solanum tuberosum
```

-continued (B) STRAIN: Desiree
(F) TISSUE TYPE: Leaf (ix) FEATURE:
(A) NAME/KEY: misc_feature
(B) LOCATION:1429..1720
(D) OTHER INFORMATION:/function= "Teil der Leader-Sequenz der cy-FBPase"

(ix) FEATURE:
(A) NAME/KEY: promoter
(B) LOCATION:1..1428

(ix) FEATURE:
(A) NAME/KEY: misc_feature
(B) LOCATION:1429
(D) OTHER INFORMATION:/function= "Transkriptionsstart"

(ix) FEATURE:
(A) NAME/KEY: TATA_signal
(B) LOCATION:1399..1405

(ix) FEATURE:
(A) NAME/KEY: CAAT_signal
(B) LOCATION:1288..1300

(xi) SEQUENCE DESCRIPTION: SEQ ID NO: 1:

```
CCAGCTAATG CTGCTCTTGT CACTCAAAAT GATGGTATCC CTCTCGTCAT CCAGTGTTTG     60
TCAAGTCCTG TTAGGAACAC AGTAAGGATA TAAACAAACA TTTTGTGGTC TTCTTGGTTA    120
TTGAGTGCTT GCTGTTCACT TGTTAAAATT GCACATATAC GTAGTGAGAA ACTCAACTGT    180
TGAGTACCAT TGATCCGTCA ATCTTGTCGA TAACTTTGAT AAGGATATTT CAGGCATCAG    240
ACATGTCACC TCTATAGAAC TTGGTCTTTT TTTTTAAAAA TAAAAATAAA AATGTTTGGC    300
ATCATACGAA CTTCTGTTAC TTTAGGCTGT ATCCAGAATA AAATGTTGTT TCCTCATTCT    360
GGAATTAGTT GTTTTGCACA CGGAAGACTT TCGAAATTTA CTAATTGTGT TCGTCCGTCT    420
CAAACTGGCT CACACTTTGG TGGTCAATTT TACTTCTCAA GGTAAGCAAT TACAGAATAT    480
GAATGTCGCT CTCCTCATAT TTATCCGAAC AATAAAAAAT GATATCTGTT TGCATATGCA    540
TGTAGATCAC ACACCCCCCC CCCCCCCGCC CCTAGATTCC CTCGATTTAG ATTAAATATA    600
ATCATCTACA AGAATTCCGT TGGGCTTCAT TATGTGTTTT TACATATTCG TTTCTGAACC    660
ACCCCCACCC CGGTGAAAAA CATTGCTCTG CCACTGGCTC AATGTATTGA CACAAATGAA    720
CTTCAAACTG GGCAGGTGAA TTATGCTCTA GGAGCATTGT ATTATCTATG CAATGCATCA    780
AACAAGGAAG AGATCTTAAA GCCAGAAGTA ATTGATGCAA TCAAAAGTTA TGCAGCTGCA    840
GGTGGAGTTA GTACAAGCTT CAGTAATTTG GCTCAGGCTT TCTTAGATCA ACATGTTCCT    900
CAGCTTAATT AAAATGGAGG AAACCAAAGA TTATGTTGTA AAATCATTTT CTATCCTAGA    960
TGGTCTATCG GAAACAATTT ATTTATTACT CCTATCCAAT TCATTATATT TTCAAAAGTT   1020
ATGAAGTCCA CGAAATATGT GACGTGGGTA AAGAAGACCC ATGCCAAGCC AGTGGGATAT   1080
AGAAACAAAA CATGTAATAA AGAGAACAAA TAATGAGTTT CGAAAAGAAC AGAAGTTAGC   1140
ATAAGGACGA GAATCACATT ATCTTAGGTG CCAACCACTA ATCCTATGTA TCATTCTCCT   1200
CTTTCCACGT GTCATCCTAC ACTTCCTTTG CCATCAGATT AGATAGCCCG GTTAGTACCT   1260
ACACTGTATA TCAAAAAATA CGTAACAATC ATCCAAACAT ATCATCGATC AAAGGATATT   1320
TATCTTGATG TGCTTTCGCC GTCCATTGTA ACGAGTTTGG ATGAATTTGA TATACACCCA   1380
CTCAGATATC AATATATTTT ATAAAAAGAA ACAAAATTGA ATACTAGTAA TATCTATGTA   1440
GATATTTATT TTTTCAACAA TCCTGTAAGT TATAAGGATA ACTCACTTAT ATGTGACGTG   1500
GATAATGAAG AGCTAGGCAG GCAGTGAGAG ATAGAAACAA ATTAAGCAGA GACGAAAAAC   1560
```

-continued

```
AAATCAGTTA ACAGAATGAC GAATTGGATC ACGCTTTATC TTAGTGCCAA CCACTGATCC   1620

CATGCATCAC TCTGCTCTTT CCACGTGGCA TCCTCTGACG TCAGATCAGA TTCCTCTTCT   1680

TTCTTTTTTT TTTCTGTATA TATATGAGCA TTTTAGTAGT                         1720
```

(2) INFORMATION FOR SEQ ID NO: 2:

(i) SEQUENCE CHARACTERISTICS:
(A) LENGTH: 1724 base pairs
(B) TYPE: nucleic acid
(C) STRANDEDNESS: double
(D) TOPOLOGY: linear (ii) MOLECULE TYPE: DNA (genomic)

(iii) HYPOTHETICAL: NO (iv) ANTI-SENSE: NO (vi) ORIGINAL SOURCE:
(A) ORGANISM: Solanum tuberosum
(B) STRAIN: Desiree
(F) TISSUE TYPE: Leaf (ix) FEATURE:
(A) NAME/KEY: misc_feature
(B) LOCATION:1433..1724
(D) OTHER INFORMATION:/function= “Teil der Leader-Sequenz der cy-FBPase”

(ix) FEATURE:
(A) NAME/KEY: misc_feature
(B) LOCATION:1..6
(D) OTHER INFORMATION:/function= “BamHI Restriction Site”

(xi) SEQUENCE DESCRIPTION: SEQ ID NO: 2:

```
GGATCCAGCT AATGCTGCTC TTGTCACTCA AAATGATGGT ATCCCTCTCG TCATCCAGTG     60

TTTGTCAAGT CCTGTTAGGA ACACAGTAAG GATATAAACA AACATTTTGT GGTCTTCTTG    120

GTTATTGAGT GCTTGCTGTT CACTTGTTAA AATTGCACAT ATACGTAGTG AGAAACTCAA    180

CTGTTGAGTA CCATTGATCC GTCAATCTTG TCGATAACTT TGATAAGGAT ATTTCAGGCA    240

TCAGACATGT CACCTCTATA GAACTTGGTC TTTTTTTTTA AAAATAAAAA TAAAAATGTT    300

TGGCATCATA CGAACTTCTG TTACTTTAGG CTGTATCCAG AATAAAATGT TGTTTCCTCA    360

TTCTGGAATT AGTTGTTTTG CACACGGAAG ACTTTCGAAA TTTACTAATT GTGTTCGTCC    420

GTCTCAAACT GGCTCACACT TTGGTGGTCA ATTTTACTTC TCAAGGTAAG CAATTACAGA    480

ATATGAATGT CGCTCTCCTC ATATTTATCC GAACAATAAA AAATGATATC TGTTTGCATA    540

TGCATGTAGA TCACACACCC CCCCCCCCCC CGCCCCTAGA TTCCCTCGAT TTAGATTAAA    600

TATAATCATC TACAAGAATT CCGTTGGGCT TCATTATGTG TTTTTACATA TTCGTTTCTG    660

AACCACCCCC ACCCCGGTGA AAAACATTGC TCTGCCACTG GCTCAATGTA TTGACACAAA    720

TGAACTTCAA ACTGGGCAGG TGAATTATGC TCTAGGAGCA TTGTATTATC TATGCAATGC    780

ATCAAACAAG GAAGAGATCT TAAAGCCAGA AGTAATTGAT GCAATCAAAA GTTATGCAGC    840

TGCAGGTGGA GTTAGTACAA GCTTCAGTAA TTTGGCTCAG GCTTTCTTAG ATCAACATGT    900

TCCTCAGCTT AATTAAAATG GAGGAAACCA AAGATTATGT TGTAAAATCA TTTTCTATCC    960

TAGATGGTCT ATCGGAAACA ATTTATTTAT TACTCCTATC CAATTCATTA TATTTTCAAA   1020

AGTTATGAAG TCCACGAAAT ATGTGACGTG GGTAAAGAAG ACCCATGCCA AGCCAGTGGG   1080

ATATAGAAAC AAAACATGTA ATAAAGAGAA CAAATAATGA GTTTCGAAAA GAACAGAAGT   1140

TAGCATAAGG ACGAGAATCA CATTATCTTA GGTGCCAACC ACTAATCCTA TGTATCATTC   1200
```

```
TCCTCTTTCC ACGTGTCATC CTACACTTCC TTTGCCATCA GATTAGATAG CCCGGTTAGT   1260

ACCTACACTG TATATCAAAA AATACGTAAC AATCATCCAA ACATATCATC GATCAAAGGA   1320

TATTTATCTT GATGTGCTTT CGCCGTCCAT TGTAACGAGT TTGGATGAAT TTGATATACA   1380

CCCACTCAGA TATCAATATA TTTTATAAAA AGAAACAAAA TTGAATACTA GTAATATCTA   1440

TGTAGATATT TATTTTTTCA ACAATCCTGT AAGTTATAAG GATAACTCAC TTATATGTGA   1500

CGTGGATAAT GAAGAGCTAG GCAGGCAGTG AGAGATAGAA ACAAATTAAG CAGAGACGAA   1560

AAACAAATCA GTTAACAGAA TGACGAATTG GATCACGCTT TATCTTAGTG CCAACCACTG   1620

ATCCCATGCA TCACTCTGCT CTTTCCACGT GGCATCCTCT GACGTCAGAT CAGATTCCTC   1680

TTCTTTCTTT TTTTTTTCTG TATATATATG AGCATTTTAG TAGT                    1724
```

(2) INFORMATION FOR SEQ ID NO: 3:

(i) SEQUENCE CHARACTERISTICS:
(A) LENGTH: 1109 base pairs
(B) TYPE: nucleic acid
(C) STRANDEDNESS: double
(D) TOPOLOGY: linear (ii) MOLECULE TYPE: DNA (genomic)

(iii) HYPOTHETICAL: NO (iv) ANTI-SENSE: NO (vi) ORIGINAL SOURCE:
(A) ORGANISM: Solanum tuberosum
(B) STRAIN: Desiree
(F) TISSUE TYPE: Leaf (ix) FEATURE:
(A) NAME/KEY: misc_feature
(B) LOCATION:1..6
(D) OTHER INFORMATION:/function= "EcoRI Restriction Site"

(xi) SEQUENCE DESCRIPTION: SEQ ID NO: 3:

```
GAATTCCGTT GGGCTTCATT ATGTGTTTTT ACATATTCGT TTCTGAACCA CCCCCACCCC     60

GGTGAAAAAC ATTGCTCTGC CACTGGCTCA ATGTATTGAC ACAAATGAAC TTCAAACTGG    120

GCAGGTGAAT TATGCTCTAG GAGCATTGTA TTATCTATGC AATGCATCAA ACAAGGAAGA    180

GATCTTAAAG CCAGAAGTAA TTGATGCAAT CAAAAGTTAT GCAGCTGCAG GTGGAGTTAG    240

TACAAGCTTC AGTAATTTGG CTCAGGCTTT CTTAGATCAA CATGTTCCTC AGCTTAATTA    300

AAATGGAGGA AACCAAAGAT TATGTTGTAA AATCATTTTC TATCCTAGAT GGTCTATCGG    360

AAACAATTTA TTTATTACTC CTATCCAATT CATTATATTT TCAAAAGTTA TGAAGTCCAC    420

GAAATATGTG ACGTGGGTAA AGAAGACCCA TGCCAAGCCA GTGGGATATA GAAACAAAAC    480

ATGTAATAAA GAGAACAAAT AATGAGTTTC GAAAAGAACA GAAGTTAGCA TAAGGACGAG    540

AATCACATTA TCTTAGGTGC CAACCACTAA TCCTATGTAT CATTCTCCTC TTTCCACGTG    600

TCATCCTACA CTTCCTTTGC CATCAGATTA GATAGCCCGG TTAGTACCTA CACTGTATAT    660

CAAAAAATAC GTAACAATCA TCCAAACATA TCATCGATCA AAGGATATTT ATCTTGATGT    720

GCTTTCGCCG TCCATTGTAA CGAGTTTGGA TGAATTTGAT ATACACCCAC TCAGATATCA    780

ATATATTTTA TAAAAAGAAA CAAAATTGAA TACTAGTAAT ATCTATGTAG ATATTTATTT    840

TTTCAACAAT CCTGTAAGTT ATAAGGATAA CTCACTTATA TGTGACGTGG ATAATGAAGA    900

GCTAGGCAGG CAGTGAGAGA TAGAAACAAA TTAAGCAGAG ACGAAAAACA AATCAGTTAA    960

CAGAATGACG AATTGGATCA CGCTTTATCT TAGTGCCAAC CACTGATCCC ATGCATCACT   1020
```

-continued

```
CTGCTCTTTC CACGTGGCAT CCTCTGACGT CAGATCAGAT TCCTCTTCTT TCTTTTTTTT  1080

TTCTGTATAT ATATGAGCAT TTTAGTAGT                                    1109
```

(2) INFORMATION FOR SEQ ID NO: 4:

(i) SEQUENCE CHARACTERISTICS:
(A) LENGTH: 1428 base pairs
(B) TYPE: nucleic acid
(C) STRANDEDNESS: double
(D) TOPOLOGY: linear (ii) MOLECULE TYPE: DNA (genomic)

(iii) HYPOTHETICAL: NO (iv) ANTI-SENSE: NO (vi) ORIGINAL SOURCE:
(A) ORGANISM: Solanum tuberosum
(B) STRAIN: Desiree
(F) TISSUE TYPE: Leaf (xi) SEQUENCE DESCRIPTION: SEQ ID NO: 4:

```
CCAGCTAATG CTGCTCTTGT CACTCAAAAT GATGGTATCC CTCTCGTCAT CCAGTGTTTG    60

TCAAGTCCTG TTAGGAACAC AGTAAGGATA TAAACAAACA TTTTGTGGTC TTCTTGGTTA   120

TTGAGTGCTT GCTGTTCACT TGTTAAAATT GCACATATAC GTAGTGAGAA ACTCAACTGT   180

TGAGTACCAT TGATCCGTCA ATCTTGTCGA TAACTTTGAT AAGGATATTT CAGGCATCAG   240

ACATGTCACC TCTATAGAAC TTGGTCTTTT TTTTTAAAAA TAAAAATAAA AATGTTTGGC   300

ATCATACGAA CTTCTGTTAC TTTAGGCTGT ATCCAGAATA AAATGTTGTT TCCTCATTCT   360

GGAATTAGTT GTTTTGCACA CGGAAGACTT TCGAAATTTA CTAATTGTGT TCGTCCGTCT   420

CAAACTGGCT CACACTTTGG TGGTCAATTT TACTTCTCAA GGTAAGCAAT TACAGAATAT   480

GAATGTCGCT CTCCTCATAT TTATCCGAAC AATAAAAAAT GATATCTGTT TGCATATGCA   540

TGTAGATCAC ACACCCCCCC CCCCCCCGCC CCTAGATTCC CTCGATTTAG ATTAAATATA   600

ATCATCTACA AGAATTCCGT TGGGCTTCAT TATGTGTTTT TACATATTCG TTTCTGAACC   660

ACCCCCACCC CGGTGAAAAA CATTGCTCTG CCACTGGCTC AATGTATTGA CACAAATGAA   720

CTTCAAACTG GGCAGGTGAA TTATGCTCTA GGAGCATTGT ATTATCTATG CAATGCATCA   780

AACAAGGAAG AGATCTTAAA GCCAGAAGTA ATTGATGCAA TCAAAAGTTA TGCAGCTGCA   840

GGTGGAGTTA GTACAAGCTT CAGTAATTTG GCTCAGGCTT TCTTAGATCA ACATGTTCCT   900

CAGCTTAATT AAAATGGAGG AAACCAAAGA TTATGTTGTA AAATCATTTT CTATCCTAGA   960

TGGTCTATCG GAAACAATTT ATTTATTACT CCTATCCAAT TCATTATATT TTCAAAAGTT  1020

ATGAAGTCCA CGAAATATGT GACGTGGGTA AAGAAGACCC ATGCCAAGCC AGTGGGATAT  1080

AGAAACAAAA CATGTAATAA AGAGAACAAA TAATGAGTTT CGAAAAGAAC AGAAGTTAGC  1140

ATAAGGACGA GAATCACATT ATCTTAGGTG CCAACCACTA ATCCTATGTA TCATTCTCCT  1200

CTTTCCACGT GTCATCCTAC ACTTCCTTTG CCATCAGATT AGATAGCCCG GTTAGTACCT  1260

ACACTGTATA TCAAAAAATA CGTAACAATC ATCCAAACAT ATCATCGATC AAAGGATATT  1320

TATCTTGATG TGCTTTCGCC GTCCATTGTA ACGAGTTTGG ATGAATTTGA TATACACCCA  1380

CTCAGATATC AATATATTTT ATAAAAAGAA ACAAAATTGA ATACTAGT               1428
```

(2) INFORMATION FOR SEQ ID NO: 5:

(i) SEQUENCE CHARACTERISTICS:

-continued

```
        (A) LENGTH: 817 base pairs
        (B) TYPE: nucleic acid
        (C) STRANDEDNESS: double
        (D) TOPOLOGY: linear

    (ii) MOLECULE TYPE: DNA (genomic)

   (iii) HYPOTHETICAL: NO

    (iv) ANTI-SENSE: NO

    (vi) ORIGINAL SOURCE:
        (A) ORGANISM: Solanum tuberosum
        (B) STRAIN: Desiree
        (F) TISSUE TYPE: Leaf

    (ix) FEATURE:
        (A) NAME/KEY: misc_feature
        (B) LOCATION:1..6
        (D) OTHER INFORMATION:/function= "EcoRI Restriction Site"

    (xi) SEQUENCE DESCRIPTION: SEQ ID NO: 5:

GAATTCCGTT GGGCTTCATT ATGTGTTTTT ACATATTCGT TTCTGAACCA CCCCCACCCC      60

GGTGAAAAAC ATTGCTCTGC CACTGGCTCA ATGTATTGAC ACAAATGAAC TTCAAACTGG     120

GCAGGTGAAT TATGCTCTAG GAGCATTGTA TTATCTATGC AATGCATCAA ACAAGGAAGA     180

GATCTTAAAG CCAGAAGTAA TTGATGCAAT CAAAAGTTAT GCAGCTGCAG GTGGAGTTAG     240

TACAAGCTTC AGTAATTTGG CTCAGGCTTT CTTAGATCAA CATGTTCCTC AGCTTAATTA     300

AAATGGAGGA AACCAAAGAT TATGTTGTAA AATCATTTTC TATCCTAGAT GGTCTATCGG     360

AAACAATTTA TTTATTACTC CTATCCAATT CATTATATTT TCAAAAGTTA TGAAGTCCAC     420

GAAATATGTG ACGTGGGTAA AGAAGACCCA TGCCAAGCCA GTGGGATATA GAAACAAAAC     480

ATGTAATAAA GAGAACAAAT AATGAGTTTC GAAAAGAACA GAAGTTAGCA TAAGGACGAG     540

AATCACATTA TCTTAGGTGC CAACCACTAA TCCTATGTAT CATTCTCCTC TTTCCACGTG     600

TCATCCTACA CTTCCTTTGC CATCAGATTA GATAGCCCGG TTAGTACCTA CACTGTATAG     660

CAAAAAATAC GTAACAATCA TCCAAACATA TCATCGATCA AAGGATATTT ATCTTGATGT     720

GCTTTCGCCG TCCATTGTAA CGAGTTTGGA TGAATTTGAT ATACACCCAC TCAGATATCA     780

ATATATTTTA TAAAAAGAAA CAAAATTGAA TACTAGT                             817
```